United States Patent [19]

Shigematsu et al.

[11] Patent Number: 4,847,015
[45] Date of Patent: Jul. 11, 1989

[54] PROCESS FOR PRODUCING EGG YOLK LECITHIN HAVING REDUCED PE CONTENT AND/OR CONTAINING SUBSTANTIALLY NO IMPURITIES

[75] Inventors: Yasuhiko Shigematsu; Mineo Hasegawa, both of Tokyo, Japan

[73] Assignee: Kewpie Kabushiki Kaisha, Tokyo, Japan

[21] Appl. No.: 123,113

[22] PCT Filed: Feb. 6, 1987

[86] PCT No.: PCT/JP87/00077
§ 371 Date: Oct. 7, 1987
§ 102(e) Date: Oct. 7, 1987

[87] PCT Pub. No.: WO87/04711
PCT Pub. Date: Aug. 13, 1987

[30] Foreign Application Priority Data

Feb. 10, 1986 [JP] Japan ................................ 61-27099
Feb. 3, 1987 [JP] Japan ................................ 62-23242

[51] Int. Cl.$^4$ ............................ C07F 9/00; C07F 9/10
[52] U.S. Cl. ................................ 260/403; 260/412.4; 260/427; 260/428; 260/428.5
[58] Field of Search .................... 260/403, 412.4, 427, 260/428, 428.5

[56] References Cited

U.S. PATENT DOCUMENTS 2,864,848 12/1958 McArthur ............................ 260/403
4,629,588 12/1986 Welsh et al. ........................ 260/428

FOREIGN PATENT DOCUMENTS 0043018 1/1982 European Pat. Off. ............ 260/403
0054770 6/1982 European Pat. Off. ............ 260/403
0115981 8/1984 European Pat. Off. ............ 260/403
0217765 4/1987 European Pat. Off. ............ 260/403
1588863 4/1970 France ................................ 260/403
1191689 8/1986 Japan .................................. 260/403

*Primary Examiner*—Patrick P. Garvin
*Assistant Examiner*—E. D. Irzinski
*Attorney, Agent, or Firm*—Oblon, Spivak, McClelland, Maier & Neustadt

[57] ABSTRACT

This invention provides a process for producing egg yolk lecithin having reduced PE (phosphatidylethanolamine) content and/or containing substantially no impurities. The characteristic features of the invention are that it has ensured the production of egg yolk lecithin containing substantially no impurities while having a low PE content or containing substantially no PE in a high yield on a commercial scale by dissolving the starting-material egg yolk lecithin in a polar solvent or a mixture of a polar solvent and a non-polar solvent and thereafter contacting the resultant solution with an ion exchange resin to thereby cause the resin to selectively and efficiently adsorb and remove impurities predominantly comprising inorganic salts and free amino acids derived from the starting material and substantially only PE in the lipid components therein, and also the production of egg yolk lecithin containing substantially no impurties while retaining the PE content substantially at the initial level from the starting-material egg yolk lecithin on a commercial scale by controlling the quantity of the ion exchange resin to be used in the practice of the above process.

11 Claims, No Drawings

PROCESS FOR PRODUCING EGG YOLK LECITHIN HAVING REDUCED PE CONTENT AND/OR CONTAINING SUBSTANTIALLY NO IMPURITIES

TECHNICAL FIELD

The present invention relates to a novel process for producing egg yolk lecithin having reduced phosphatidylethanolamine (herein abbreviated to PE) content and/or containing substantially no impurities.

BACKGROUND ART

Heretofore, a lipid fraction derived from egg yolk and containing phospholipids, typically phosphatidylcholine (herein abbreviated to PC), namely, the so-called egg yolk lecithin, is widely used in the field of cosmetics or pharmaceutical products as an emulsifier or a liposome-forming agent as a carrier for drugs by virtue of the surface activity, permeating effect and other properties of the phospholipids contained therein.

It so happens that PC has the structure of cylindrical molecules comprising balanced sizes of hydrophobic and hydrophilic groups, and when egg yolk lecithin with a high PC content is used as a liposome-forming agent, it is therefore capable of forming a liposome having a stable lipid bilayer. If egg yolk lecithin with a high PC content and yet a low PE content is used in this case, it is possible to produce a liposome having higher structural stability, i.e., a strong and pliant membrane. When used as a starting material for cosmetics such egg yolk lecithin with a high PC content and a low PE content is also capable of stabilizing various physical properties of the end product.

In view of the above, if egg yolk lecithin with reduced PE content and relatively increased PC content could be produced, such egg yolk lecithin would be highly beneficial from a commercial point of view.

Egg yolk lecithin (lipid fraction) obtained by extraction from egg yolk by a conventional method essentially comprises phospholipids, such as PC and PE, and neutral lipids, such as triglyceride and cholesterol.

Various methods for fractionation of phospholipids from the egg yolk lecithin have heretofore been known in the art. For example, Japanese Patent Laid-Open Pub. No. 152392/1984 discloses a method wherein a solution of a lipid fraction dissolved in a non-polar or weakly polar solvent is brought into contact with a resin which adsorbs phospholipids preferentially to cuase the resin to adsorb the phospholipids, and thereafter the phospholipids thus adsorbed are eluted with a polar solvent. In accordance with this method, it is possible to obtain phospholipid fractions having different PE to PC ratios by collecting the eluates according to fractions. However, a fraction having a high PC content and a low PE content can be obtained only at an exceedingly low proportional rate (about 10%) for the starting lipid fraction to be treated, and yet copious quantities (about 200-fold (v/v) volume) of the resin is required for the starting material. It is therefore difficult to fractionate by this method phospholipids having a high PC content and alow PE content economically on a commercial scale.

Furthermore, various methods for increasing the PC component in egg yolk lecithin have been attempted so far. For example, solvent fractionation which comprises adding water to egg yolk lecithin dissolved in ethanol thereby to precipitate PE has been known in the art. This method, however, is accompanied by a problem in that an increase in PC content results in a notably low yield of the end product. As another example, a method using an adsorbent such as silica gel or alumina has been known in the art. This method, however, entails some difficulties when it is practiced on a commercial scale such as that the yield of the end product is low although PC and PE can be fractioned from each other effectively and that the adsorbent is required in great quantities. Still another example of such known methods comprises forming a metal salt complex with Cd, Ca, Mg, Zn or the like and utilizing the solubility thereof. However, this method is again accompanied by the problem of the metal remaining inevitably in the end product obtained.

Under such circumstances, a primary object of the present invention is to provide a process whereby egg yolk lecithin with reduced PE content and relatively increased PC content can be produced in a high yield on a commercial scale.

DISCLOSURE OF THE INVENTION

As a result of extensive research effort expended toward attaining the above object, we have found that, if egg yolk lecithin is dissolved in a polar solvent or a mixture of a polar solvent and a non-polar solvent and thereafter brought into contact with an ion exchange resin, the ion exchange resin will adsorb and remove substantially only PE in the lipid components selectively and efficiently, and thus we have arrived at the present invention on the basis of this finding.

More specifically, the present invention, in one aspect thereof, provides a process for producing egg yolk lecithin with reduced PE content which comprises dissolving egg yolk lecithin in a polar solvent or a mixture of a polar solvent and a non-polar solvent, contacting the solution obtained with an ion exchanger, and then distilling off the solvent from the solution.

We have examined the egg yolk lecithin thus obtained from the point of view of the content of the residual impurities predominantly comprising inorganic salts and free amino acids derived from the starting material and have unexpectedly found that substantially no such impurities are detectable.

Thus, the present invention, in another aspect thereof, provides a process for producing as the end product egg yolk lecithin having reduced PE content and containing substantially no impurities by carrying out the above described process of the present invention with the use of crude egg yolk lecithin containing inorganic salts and free amino acids as major impurities or semipurified egg yolk lecithin as a starting material.

As a result of extended research, we have further found that the effect of removing PE as well as impurities is proportionate mainly to the quantity of the ion exchange resin used and that PE is removed after the impurities have been removed substantially completely.

The present invention, in still another aspect thereof, can thus be said to provide a process for producing as the end product egg yolk lecithin containing substantially no impurities by the above described process of the present invention with the use of crude egg yolk lecithin or semipurified egg yolk lecithin as a starting material.

BRIEF DESCRIPTION OF THE DRAWINGS

In the drawings:

FIGS. 1, 2 and 3 are graphs respectively showing the results of the tests conducted in Example 6, 7 and 8.

THE BEST MODE FOR CARRYING OUT THE INVENTION

The present invention will now be described in detail.

The starting-material egg yolk lecithin to which the process of the present invention is applicable is a lipid fraction containing phospholipids predominantly comprising PC and obtained from egg yolk by a conventional method, for example, by solvent extraction with ethanol, dichloromethane, hexane or ether. This lipid fraction is intended to include a fraction containing inorganic salts (e.g., salts of sodium, potassium, calcium, magnesium and iron) and free amino acids as primary impurities (crude egg yolk lecithin), a fraction with reduced content of impurities obtained by subjecting crude egg yolk lecithin to filtration through diatomaceous earth or a membrane filter (semipurified egg yolk lecithin), and a fraction with increased phospholipids content obtained by treating crude egg yolk lecithin or semipurified egg yolk lecithin with acetone and the like in accordance with a conventional method (egg yolk lecithin with increased phospholipids content).

The solvent for egg yolk lecithin used in the process of the present invention is a polar solvent, such as methanol, ethanol, acetone, dichloromethane or water, or a mixture thereof with a non-polar solvent, such as n-peptane, n-hexane, n-heptane, chloroform, ethyla acetate, ether or benzene. As will be apparent from the results of the test examples which will be described later, a non-polar solvent alone cannot effectively remove PE and impurities. While the mixing ratio between the polar sovlent and the non-polar solvent in the solvent mixture is not particularly limited, it is generally preferable that the proportion of the polar solvent be higher.

The concentration of the egg yolk lecithin in the solvent, i.e., the concentration of the egg yolk lecithin in the solution obtained, is preferably about 0.5 to 20% (v/v). A concentration below 0.5% is not economical because an excessively great quantity of solvent is required. If the concentration exceeds 20%, the solution will become more viscous and therefore cannot be readily brought into contact with the ion exchange resin in the subsequent step.

The ion exchange resin used herein is not particularly limited, and commercially available strongly or weakly acidic cationic exchange resins or strongly or weakly basic anionic exchange resins are suitable.

Specific examples of strongly acidic resins are Amberlite IR 120B and 200C (supplied by Rohm & Haas Co.); Dowex 50W and MSC-1 (supplied by Dow Chemical Co.); DuoLite C-20 and C-25D (supplied by Diamond Shamrock Corp.); and Lewatit S-100 and SP-120 (supplied by Farbenfabriken Bayer AG), while specific examples of weakly acidic resins are Amberlite IRC 50 and IRC 84; Dowex CCR-2; DuoLite CC-4; and Lewatit CNP-80. Strongly basic resins, on the other hand, include Amberlite IRA 400 and IRA 900; Dowex 1 and MSA-1; DuoLite A-101D; and Lewatit M-500 and MP-500, while weakly basic resins include Amberlite IRA 68 and IRA 45; and Lewatit MP-62. There resins may be used singly or may also be used either in the form of a mixture of two or more members irrespective of the species in any ratio or sequentially. For example, a mixture of one acidic resin and one basic resin in a ratio of 1:3 to 2:1 is used. Advantageously, the acidic resin is prepared in H form while the basic resin is prepared in OH form in practice in order to improve adsorption efficiency.

The quantity of the ion exchange resin used can vary depending upon the quantity of the PE and impurities contained in the starting-material egg yolk lecithin or the particular type of the resin selected. In general, however, the ion exchange resin may advantageously be used ordinarily in a volumetric quantity at least threefold the volume of the PE contained in the starting material egg yolk lecithin since the resin in less than threefold volumes is insufficient to afford the effect of removing the PE and impuritites. Preferably, the volumetric quantity of the ion exchange resin is suitably selected in the range of form 4.0- to 40-fold the volumes of the PE and impurities in the starting material. Within this range, it is possible to reduce the PE content to 2% or less which is defined as the maximum commercially permissible residual PE content to trace amounts and also to remove impurities substantially completely. Thus, the use of the resin in excess is not economical.

Since the PE is removed after the impurities have been removed substantially completely, it is possible to produce egg yolk lecithin containing substantially no impurities while retaining the PE content substantially at the level of that of starting material by controlling the quantity of the ion exchange resin to be used in the practice of the process of the present invention with the use of crude or semipurified egg yolk lecithin as a starting material. In this case, the ion exchange resin may be advantageously used in a volumetric quantity ordinarily at least 0.2-fold the volume of the startingmaterial crude or semipurified egg yolk lecithin since the resin in less than 0.2-fold volumes is insufficient to afford the effect of removing the impurities. Preferably, the volumetric quantity of the ion exchange resin is suitably selected in the range of from 0.3- to 3.0-fold the volume of the starting material depending on the quantity of the impurities contained therein. If the resin is used in excess, the PE will also be removed.

The egg yolk lecithin solution may be brought into contact with the ion exchange resin by passing the solution through a columnpacked with a predetermined quantity of the resin by a conventional method or by supending a predetermined quantity of the resin in the solution with stirring. This contact is advantageously carried out at a temperature lower than the boiling point of the solvent from the point of view of the prevention of the evaporation of the solvent.

In accordance with the process of the present invention, after the PE and/or impurities have been caused to be selectively adsorbed on the ion exchange resin by the above described contact, the solvent used is distilled off, for example, under reduced pressure, from the solution subsequently to the selective adsorption in the case where the solution has been passed through the column, or after the resin has been removed, for example, by filtration in the case where the solution has been contacted with the resin by stirring.

According to the process of the present invention as has been described hereinabove, the PE content in the starting-material egg yolk lecithin can be reduced very effectively and hence egg yolk lecithin with relatively increased PC content and containing substantially no impurities can be produced. In addition, as will be apparent from the results of the experimental examples, which will be described later, the PE content in the starting-material egg yolk lecithin can be reduced to almost one half with the use of the ion exchange resin in a quantity about 3-fold (v/v) the intital PE content. That is, only an extremely small quantity of resin is required and, because the resin selectively adsorbs and removes impurities and substantially only PE in the lipid components, the end product can be obtained in a good yield. Thus, egg yolk lecithin containing substantially no impurities while having an increased PC content and containing less or substantially no PE can be produced on a commercial scale. Needless to say, the process of the present invention, if repeatedly practiced, can be carried out more suitably for the desired purpose.

Further, according to the process of this invention, egg yolk lecithin containing substantially no impurities while retaining the PE content substantially at the level of that of the starting-material egg yolk lecithin used can be produced on a commercial scale by a remarkably simple procedure by suitably controlling the quantity of the ion exchange resin to be used.

The advantageous effects of the present invention will now be discussed in greater detail with reference to the results of experimental examples, it being understood that all percentages set forth herein are % by weight unless otherwise indicated and that both the egg yolk lecithin and PE have a specific gravity of approximately 1.

EXPERIMENTAL EXAMPLE 1

This Experimental Example shows how the effect of removing PE and impurities according to the process of the present invention varies depending on the species of the solvent used.

20g each of previously prepared egg yolk lecithin (PC; 58.0%, PE; 10.0%) was dissolved respectively in 200 ml of absolute ethanol, n-hexane, chloroform, ethyl acetate, 95% ethanol, and a chloroform-methanol-water (10:10:1) solution mixture. Each of the solutions obtained was passed through a column packed with a mixture of 10 ml each of Amberlite IR 120B (H type) and Amberlite IRA 400 (OH type) by a conventional method. The solvent used was then completely distilled off from each solution under reduced pressure to obtain the end-product egg yolk lecithin sample.

With respect to each sample thus obtained, the residual PE content was measured by means of IATROSCAN Model TH-10; the quantity of the impurities was determined by atomic absorption analysis in terms of metal ions; and further quantity of free amino acids was determined by amino acid analysis. The results obtained are summarized in TABLE 1 below.

TABLE 1

|  | Solvent | Residual PE content (%) | Metal ion (mg %) | Free amino acid (mg %) | Electric conductivity (μS/cm) |
|---|---|---|---|---|---|
| Polar solvent | Absolute ethanol | 0.3 | 80 | 15 | 7.3 |
|  | 95% Ethanol | ≦0.1 | 68 | 12 | 5.9 |
| Polar solvent/non-polar solvent mixture | Chloroform-methanol-water (10:10:1) | ≦0.1 | 120 | 25 | 10.3 |
| Non-polar solvent | n-Hexane | 8.7 | 750 | 480 | 560 |
|  | Chloroform | 8.7 | 900 | 390 | 610 |
|  | Ethyl acetate | 9.0 | 1,050 | 450 | 700 |

Notes:
1. The starting-material egg yolk lecithin contained as impurities 1,100 mg% of metal ions and 500 mg% of free amino acids while having an electric conductivity of 720 μS/cm.
2. As one index of the content of impurities, the results of the measurement of the electric conductivity obtained for 5 w/v% emulsion of each sample are also shown in the TABLE.

As is apparent from the above data, the contents of PE and impurities in the starting-material egg yolk lecithin can be reduced very effectively when a polar solvent or a mixture of a polar solvent and a non-polar solvent is used while, on the other hand, neither PE nor impurities can be removed effectively when a non-polar solvent alone is used.

EXPERIMENTAL EXAMPLE 2

This Experimental Example demonstrates that, in accordance with the process of the present invention, PE can be removed effectively with the use of an exceedingly small quantity of ion exchange resin.

20g (PE content: 4.0g) each of previously prepared egg yolk lecithin (PC: 78.2%, PE: 20.0%) was dissolved in 180 ml of 95% ethanol. Each of the solutions obtained was passed through a column packed respectively with 2 ml, 4 ml, 6 ml, 8 ml, 10 ml, 12 ml, 14 ml, 16 ml and 20 ml of a mixture of Dowex 50W (H type) and Dowex 1 (OH type) in equal quantity by a conventional method. The solvent used was then completely distilled off from each solution under reduced pressure to obtain the end-product egg yolk lecithin sample.

Subsequently, the residual PE content in each sample thus obtained was measured by means of IATROSCAN Model TH-10. The results are listed in the following Table 2.

TABLE 2

| Quantity of resin (ml) | PE Content (g) |
|---|---|
| 2 | 3.9 |
| 4 | 3.6 |
| 6 | 3.1 |
| 8 | 2.5 |
| 10 | 2.2 |
| 12 | 1.9 |
| 14 | 1.5 |
| 16 | 1.3 |
| 20 | 1.1 |

As is noted from the above data, the PE contact in the starting-material egg yolk lecithin can be reduced to almost one half with the use of the resin in a quantity about 3-fold (v/v) the initial PE content, and thus only an extremely small quantity of resin is required in the process of the present invention.

EXPERIMENTAL EXAMPLE 3

This Experimental Example shows how the effect of removing impurities varies depending on the species of the solvent used in the case where only the impurities are intended to be removed by controlling the quantity of the ion exchange resin used in the process of the present invention.

20g each of previously prepared egg yolk lecithin (PC; 79.2%, PE: 20.0%, metal ions: 1,100 mg%, free amino acids: 800 mg%) was dissolved respectively in 200 ml of ether, n-hexane, 95% ethanol, a chloroform-methanol (2:1) solution mixture, and an n-hexane-acetone (2:1) solution mixture. To each of the solutions obtained were added 2 ml of Amberlite IR 120B (H type) and 3 ml of Amberlite IRS 400 (OH type). The resulting solution was stirred for 30 minutes and then filtered to remove the ion exchange resins. The solvent used was thereafter completely distilled off from each solution under reduced pressure to obtain the end-product egg yolk lecithin sample.

Subsquently, 5 w/v% emulsion of each sample was perpared, and the electric conductivity thereof was measured. The results obtained are set forth in TABLE 3 below.

TABLE 3

| | Solvent | Electric conductivity ($\mu$S/cm) |
|---|---|---|
| Polar solvent | 95% Ethanol | 7.9 |
| | Chloroform-methanol (2:1) | 6.8 |
| Polar solvent/ non-polar solvent mixture | n-Hexane-acetone (2:1) | 6.4 |
| Non-polar solvent | Ether | 450 |
| | n-Hexane | 520 |

Note:
The electric conductivity of the starting-material egg yolk lecithin was 750 $\mu$S/cm.

It will be understood from the above data that the impurities in the starting material can be removed very effectively when a polar solvent or a mixture of a polar solvent and a non-polar solvent is used, whereas effective removal cannot be attained when non-polar solvent along is used.

The present invention will now be described more fully in greater detail with reference to specific examples of practice.

EXAMPLE 1

500 g of previously prepared egg yolk lecithin (PC: 56.9%, PE: 9.6%, cholesterol: 14.9%, triglyceride: 18.6%, metal ions: 960 mg%, free amino acids: 680mg%, electric conductivity: 690 $\mu$S/cm) was dissolved in 4.5 liters of 95% ethanol. The solution obtained was passed through a column packed with a mixture of 500 ml of Amberlite IR 120B (H type) and 1,000 ml of Amberlite IRA 400 (OH type) by a conventional method. The solvent used was then completely distilled off from the solution under reduced pressure to obtain 450 g of egg yolk lecithin having a PE content reduced to 1.0%. This product was found to comprise, in addition to PE, 62.0% of PC, 15.7% of cholesterol, 19.9% of triglyceride, 72 mg% of metal ions, and 59 mg% of free amino acid while having an electric conductivity of 28 $\mu$S/cm.

EXAMPLE 2

200 g of previously prepared egg yolk lecithin (PC: 79.6%, PE: 18.0%, cholesterol: 1.2%, metal ions: 1,100 mg%, free amino acids: 600 mg%, electric conductivity: 720 $\mu$S/cm) was dissolved in 2 liters of a chloroform-methanol-water (10:10:1) solution mixture. The solution obtained was passed through a column packed with a mixture of 200 ml of Dowex 50 W (H type) and 400 ml of Dowex 1 (OH type) by a conventional method. The solvent used was then completely distilled off from the solution under reduced pressure to obtain 80 g of egg yolk lecithin having a PE content reduced to 1.0%. This product was found to comprise, in addition to PE, 96.1% of PC, 1.4% of chlolesterol, 40 mg% of metal ions, and 20 mg% of free amino acid while having an electric conductivity of 12 $\mu$S/cm.

EXAMPLE 3

500 g (PE content: 16.5 g) of previously prepared egg yolk lecithin (PC: 29.6%, PE: 3.3%, cholesterol: 4.3%, triglyceride: 62.3%, metal ions: 520 mg%, free amino acids: 210 mg%, electric conductivity: 230 $\mu$S/cm) was dissolved in 4.5 liters of 99.5% ethanol. The solution obtained was passed through a column packed with a mixture of 25 ml of Lawatit S-100 (H type) and 25 ml of Lawatit M-500 (OH type) by a conventional method. The solvent used was thereafter completely distilled off from the solution under reduced pressure to obtain 490 g of egg yolk lecithin having a PE content reduced to 1.6%. This product was found to comprise, in addition to PE, 30.2% of PC, 4.5% of cholesterol, 63.1% of triglyceride, 73 mg% of metal ions, and 26 mg% of free amino acids while having an electric conductivity of 32 $\mu$S/cm.

In all of Examples 1, 2 and 3 described above, egg yolk lecithin products with the contents of PE and impurities respectively reduced to substantially the same levels could be obtained even in the case where the egg yolk lecithin solution was brought into contact with the ion exchange resin without using a column but simply by stirring.

EXAMPLE 4

100 g of previously prepared egg yolk lecithin (PC: 78.0%, PE: 18.3%, cholesterol: 2.0%, triglyceride: 0%, metal ions: 1,000 mg%, free amino acids: 700 mg%, electric conductivity: 730 $\mu$S/cm) was dissolved in a hexane-ethanol (80:20) solution mixture. To the solution obtained were added 60 ml of Amberlite IR 120B (H type) and 120 ml of Amberlite IRA 400 (OH type), and the resulting solution was stirred for mixing for 30 minutes. Subsequently, the ion exchange resins were removed from the solution by filtration, and the solvent used was completely distilled off under reduced pressure. The resultant solution was then subjected to treatment with acetone to obtain 76 g of egg yolk lecithin having a PE content of 0%. This product was found to comprise, exclusive of PE, 96.8% of PC, 1.5% of cholesterol, 50 mg% of metal ions, and 12 mg% of free amino acids while having an electric conductivity of 5.3 $\mu$S/cm.

EXAMPLE 5

2 kg of egg yolk lecithin (PC: 80.5%, PE: 17.3%, cholesterol: 0.5%, triglyceride: 0.1%, metal ions: 430 mg%, free amino acids: 180 mg%, electric conductivity: 120 $\mu$S/cm) obtained by contacting dry egg yolk with supercritical carbon dioxide to extract the fat component and subjecting the thus extracted fat component to treatment with ethanol was dissolved in a chloroform-methanol-water (10:10:1) solution mixture. To the solution obtained were added 1,000 ml of DuoLite C-20 (H type) and 2,000 ml of DuoLite A-101D (OH type), and the resulting solution was stirred for mixing for 30 minutes.

Thereafter, the ion exchange resins were removed from the solution by filtration, and the solvent used was completely distilled off under reduced pressure. The resultant solution was then subjected to treatment with acetone to obtain 1.4 kg of egg yolk lecithin having a PE content reduced to 2%. This egg yolk lecithin was found to comprise, in addition to PE, 94.2% of PC, 0.8% of cholesterol, 0.1% of triglyceride, 48 mg% of metal ions, and 16 mg% of free amino acids while having an electric conductivity of 7.3 μS/cm.

EXAMPLES 6, 7 AND 8

In the respective Examples, the crude egg yolk lecithin materials shown in TABLE 4 were dissolved in the solvents shown in the same TABLE to prepare the necessary number of solutions for each material. To the solutions thus prepared for each material were added in varying quantities the ion exchange resin mixtures shown in the same TABLE, and the resulting solutions were stirred for mixing for 30 minutes at normal temperature (20° C.). The resins used were removed by filtration, and the solvent was then completely distilled off from the respective solutions under reduced pressure to obtain egg yolk lecithin samples corresponding to the quantities of the resins used.

Subsequently, the contents of the residual PE and impurities in the samples obtained in the respective Examples were measured by the method employed in Experimental Example 1. The results obtained are shown by graphs for the respective Examples (FIGS. 1, 2 and 3).

TABLE 4

| Example | Crude egg yolk lecithin Composition | Quantity | Solvent Ratio | Quantity | Ion exchange resin Species | Ratio | Graph showing residual PE & impurities |
|---|---|---|---|---|---|---|---|
| 6 | PC:76.0% PE:20.0% Metal ions: 400 mg % Free amino acids: 300 mg % | 100 g | Hexane-methanol (80:20) | 500 ml | Amberlite IR120B (H type): Amberlite IRA400 (OH type) | 1:2 | FIG. 1 |
| 7 | PC:76.0% PE:20.0% Metal ions: 1000 mg % Free amins acids: 750 mg % | 100 g | Hexane-methanol (80:20) | 500 ml | Amberlite IR120B (H type): Amberlite IRA400 (OH type) | 1:2 | FIG. 2 |
| 8 | PC:85.4% PE:10.2% Metal ions: 1800 mg % Free amino acids: 1200 mg % | 100 g | Water-saturated dichloromethane | 1000 ml | Amberlite IR120B (H type) Amberlite IRA400 (OH·type) | 1:2 | FIG. 3 |

Example 9, 10 and 11 set forth hereinbelow are examples wherein only the impurities in the starting-material egg yolok lecithin are removed by controlling the quantity of the ion exchange resin used in the process of the present invention within a predetermined range.

EXAMPLE 9

1,200 g of previously prepared egg yolk lecithin (PC: 51.7%, PE: 10.2%, neutral lipids: 37.2%, free amino acids: 660 mg%, metal ions: 1,090 mg%, electric conductivity: 566 μS/cm) was dissolved in 12 liters of water-saturated dichloromethane. To the solution obtained were added 200 ml of Amberlite IR 120B (H type) and 400 ml of Amberlite IRA 400 (OH type), and the resulting solution was stirred for mixing for 30 minutes. Thereafter, the ion exchange resin used were removed by filtration, and the solvent was then completely distilled off under reduced pressure to obtain 1,170 g of purified egg yolk lecithin. This purified egg yolk lecithin was found to comprise 52.0% of PC, 10.0% of PE, 37.3% of neutral lipids, 37 mg% of free amino acids, and 180 mg% of metal ions while having an electric conductivity of 6.4 μS/cm.

Subsequently, the solubility of the thus obtained purified egg yolk lecithin in an organic solvent was tested in conjuction with that of the starting material. The results are presented in TABLE 5. In order to test the solubility, 10 w/v% solutions of the starting and purified egg yolk lecithin samples were prepared by using the respective solvents.

TABLE 5

| Solvent | Starting-material egg yolk lecithin | Purified egg yolk lecithin |
|---|---|---|
| Hexane | White turbidity observed | Dissolved completely and clearly |
| Chloroform | White turbidity observed | Dissolved completely and clearly |
| Ethanol | Yellowish white predipitate formed slightly | Dissolved completely and clearly |

EXAMPLE 10

500 g of previously prepared egg yolok lecithin (PC: 79.9%, PE: 16.6%, neutral lipids: 1.7%, free amino acids: 570 mg%, and metal ions: 1,100 mg% while having an electric conductivity of 750 μS/cm) was dissolved in 3 liters of an n-hexane-acetone (2:1) solution mixture. To the solution obtained were added 250 ml of Dowex 50 W (H type) and 250 ml of Dowex 1 (OH type), and the resulting solution was stirred for mixing for 15 minutes. The ion exchange resins used were then removed by filtration, and thereafter the solvent was completely distilled off under reduced pressure to obtain 490 g of purified egg yolk lecithin. This purified egg yolk lecithin was found to comprise 79.8% of PC, 16.4% of PE, 1.8% of neutral lipids, 0 mg% of free amino acids, and 127 mg% of metals while having an electric conductivity of 29 μS/cm.

Subsequently, the solubility of the thus obtained purified lecithin in an organic solvent was tested in accordance with the procedure of the preceding Example 9 in comparision with that of the starting material. The results are set forth in TABLE 6.

TABLE 6

| Solvent | Starting-material egg yolk lecithin | Purified egg yolk lecithin |
|---|---|---|
| Hexane | Dissolved completely and clearly | Dissolved completely and clearly |
| Chloroform | Slight turbidity observed | Dissolved completely and clearly |
| Ethanol | Yellowish white precipitate formed | Dissolved completely and clearly |

EXAMPLE 11

1,000 g of previously prepared egg yolk lecithin (PC: 77.0%, PE: 17.5%, neutral lipids: 4.6%, free amino acids: 274 mg%, metal ions: 346 mg%, electric conductivity: 250 $\mu$S/cm) was dissolved in 5 liters of a chloroform-methanol-water (10:5:1) solution mixture. To the solution obtained were added 50 ml of DuoLite C-20 (H type) and 150 ml of DuoLite A-1091D (OH type), and the resulting solution was stirred for mixing for 30 minutes. Thereafter, the ion exchange resins used were removed by filtration, and the solvent was then completely distilled off under reduced pressure to obtain 980 g of purified egg yolk lecithin. This purified egg yolk lecithin was found to comprise 77.6% of PC, 16.5% of PE, 4.8% of neutral lipids, 45 mg% of free amino acids, and 190 mg% of metal ions while having an electric conductivity of 28 $\mu$S/cm.

Subsequently, the solubility of the thus obtained purified lecithin in an organic solvent was tested in accordance with the procedure of Example 9 described above in comparison with that of the starting material. The results are shown in TABLE 7 below.

TABLE 7

| Solvent | Starting-material egg yolk lecithin | Purified egg yolk lecithin |
|---|---|---|
| Hexane | White turbidity observed | Dissolved completely and clearly |
| Chloroform | Slight turbidity observed | Dissolved completely and clearly |
| Ethanol | Yellowish white precipitate formed | Dissolved completely and clearly |

INDUSTRIAL APPLICABILITY

The egg yolk lecithin obtained by the process of the present invention, in one embodiment thereof, is egg yolk lecithin having a PE content reduced to an extent wherein it has been very effectively lowered or wherein the lecithin is substantially free of PE while having a relatively increased PC content yet containing substantially no impurities, and is therefore expected to have wider application in various fields, especially in the fields of pharmaceutical products and cosmetics.

The egg yolk lecithin obtained by the process of the present invention, in anther embodiment thereof, is egg yolk lecithin retaining the PE content substantially at the level of that of the starting-material egg yolk lecithin used, i.e., retaining the phospholipid composition of the starting material, while excluding substantially only impurities, and is therefore expected to have wider application in various fields as one purified phospholipid material, for example, as an emulsifier. Especially, it has hiterto been difficult to substantially completely remove from crude egg yolk lecithin impurities such as inorganic salts, free amino acids and polypeptides, so that egg yolk lecithin does not readily dissolve in ordinary organic solvents, and thus the applicability thereof has been limited. In accordance with the process of the present invention, egg yolk lecithin containing substantially no such impurities and having remarkably improved solubility can be obtained whereby wider application of the egg yolk lecithin can be expected.

We claim:

1. A process for producing egg yolk lecithin having reduced PE (phosphatidylethanolamine) content which comprises dissolving egg yolk lecithin in a strong polar solvent or a mixture of a strong polar solvent and a non-polar solvent, contacting the solution obtained with an ion exchange resin, and then distilling off the solvent from the solution.

2. A process as claimed in claim 1, wherein the starting-material egg yolk lecithin is crude egg yolk lecithin containing inorganic salts and free amino acids as major impurities or semipurified egg yolk lecithin, and the product obtained after the distillation of the solvent off is egg yolk lecithin having reduced PE content and containing substantially no impurities.

3. A process as claimed in claim 1, wherein the starting-material egg yolk lecithin comprises phospholipids and neutral lipids as primary constituents.

4. A process as claimed in claim 1, wherein the starting-material egg yolk lecithin has a high phospholipids content.

5. A process as claimed in claims 2, 3 and 4, wherein the ion exchange resin is used in a volumetric quantity at least 3-fold the volume of the PE in the starting-material egg yolk lecithin.

6. A process as claimed in claim 5, wherein the ion exchange resin is used in a volumetric quantity in the range of from 4.0- to 40-fold the volume of said PE.

7. A process as claimed in any of claims 1 through 6, wherein the strong polar solvent is selected from methanol, ethanol, acetone, dichloromethane and water.

8. A process as claimed in any claims 1 through 7, wherein the concentration of the egg yolk lecithin in the solvent is 0.5 to 20% (v/v).

9. A process for producing egg yolk lecithin containing substantially no impurities which comprises dissolving crude egg yolk lecithin containing inorganic salts and free amino acids as major impurities or semipurified egg yolk lecithin is a strong polar solvent or a mixture of a strong polar solvent and a non-polar solvent, contacting the solution obtained with an ion exchange resin, and the distilling off the solvent from the solution.

10. A process as claimed in claim 9, wherein the ion exchange resin is used in a volumetric quantity at least 0.2-fold the volume of the starting-material crude egg yolk lecithin or semipurified egg yolk lecithin.

11. A process as claimed in claim 10, wherein the ion exchange resin is used in a volumetric quantity in the range of from 0.3- to 3.0-fold the volume of the starting-material crude egg yolk lecithin or semipurified egg yolk lecithin.

* * * * *